United States Patent
Charles

(10) Patent No.: US 7,285,107 B1
(45) Date of Patent: Oct. 23, 2007

(54) VITREORETINAL INSTRUMENT

(75) Inventor: Steven T. Charles, Memphis, TN (US)

(73) Assignee: Alcon, Inc., Hunenberg (CH)

(*) Notice: Subject to any disclaimer, the term of this patent is extended or adjusted under 35 U.S.C. 154(b) by 7 days.

(21) Appl. No.: 10/672,188

(22) Filed: Sep. 26, 2003

Related U.S. Application Data

(60) Provisional application No. 60/419,123, filed on Oct. 17, 2002.

(51) Int. Cl.
*A61M 1/00* (2006.01)

(52) U.S. Cl. .......................................... 604/35; 604/28

(58) Field of Classification Search ................ 604/335, 604/264, 506, 521, 294, 119, 140, 141, 143, 604/146, 147, 246, 290, 158, 208, 164.11, 604/27, 30, 34, 35, 36, 22, 118, 249, 250, 604/320, 902, 540, 542, 164.01, 21, 93.01, 604/181, 187; 222/389, 179; 156/365
See application file for complete search history.

(56) References Cited

U.S. PATENT DOCUMENTS

| | | | |
|---|---|---|---|
| 2,756,740 A * | 7/1956 | Deane ........................ 604/77 |
| 3,439,675 A * | 4/1969 | Cohen ........................ 604/192 |
| 3,661,144 A * | 5/1972 | Jensen et al. ................ 600/571 |
| 4,850,350 A * | 7/1989 | Jackson ................... 128/207.16 |
| 5,242,386 A * | 9/1993 | Holzer ....................... 604/22 |
| 5,246,436 A * | 9/1993 | Rowe ......................... 606/13 |
| 5,328,481 A | 7/1994 | Wang |
| 5,795,323 A * | 8/1998 | Cucin ......................... 604/22 |
| 5,830,214 A * | 11/1998 | Flom et al. .................. 606/41 |
| 6,132,390 A * | 10/2000 | Cookston et al. ........... 600/585 |
| 6,135,984 A * | 10/2000 | Dishler ...................... 604/264 |
| 6,162,187 A * | 12/2000 | Buzzard et al. ............ 600/573 |
| 6,193,714 B1 * | 2/2001 | McGaffigan et al. ......... 606/41 |
| 6,210,357 B1 | 4/2001 | Morris |
| 6,282,442 B1 * | 8/2001 | DeStefano et al. .......... 604/21 |
| 6,325,798 B1 * | 12/2001 | Edwards et al. ............. 606/41 |
| 6,413,245 B1 | 7/2002 | Yaacobi et al. |
| 6,419,654 B1 * | 7/2002 | Kadan ........................ 604/27 |
| 2004/0039253 A1 | 2/2004 | Peyman et al. |

OTHER PUBLICATIONS

Alcon 2001 Vitreoretinal Product Catalog, p. 23, item 11 "Small Gauge Retinal Needle".

* cited by examiner

*Primary Examiner*—Nicholas D. Lucchesi
*Assistant Examiner*—Laura Bouchelle
(74) *Attorney, Agent, or Firm*—W. David Lee

(57) ABSTRACT

An improved instrument for removing subretinal fluid and performing fluid exchanges in vitreoretinal surgery is disclosed. The instrument includes a cannula with a curved distal portion and a side port on the curved distal portion for aspirating subretinal fluid. The instrument also includes a second port for aspirating a second fluid from the vitreous cavity during a fluid exchange.

12 Claims, 3 Drawing Sheets

VITREORETINAL INSTRUMENT

This application claims the priority of U.S. Provisional Application No. 60/419,123 filed Oct. 17, 2002.

FIELD OF THE INVENTION

The present invention generally pertains to vitreoretinal surgery and more particularly to improved instruments suitable for subretinal fluid removal and fluid exchanges typically used in such surgeries.

DESCRIPTION OF THE RELATED ART

In a healthy human eye, the retina is physically attached to the choroid in a generally circumferential manner behind the pars plana. The vitreous humor, a transparent jelly-like material that fills the posterior segment of the eye, helps to cause the remainder of the retina to lie against, but not physically attach, to the choroid.

Sometimes a portion of the retina becomes detached from the choroid. Other times a portion of the retina may tear, allowing vitreous humor, and sometimes aqueous humor, to flow between the retina and the choroid, creating a build up of subretinal fluid. Both of these conditions result in a loss of vision.

To surgically repair these conditions, a surgeon typically inserts a vitrectomy probe into the posterior segment of the eye via a scleratomy, an incision through the sclera at the pars plana. The surgeon typically also inserts a fiber optic light source and an infusion cannula into the eye via similar incisions, and may sometimes substitute an aspiration probe for the vitrectomy probe. While viewing the posterior segment under a microscope and with the aid of the fiber optic light source, the surgeon cuts and aspirates away vitreous using the vitrectomy probe to gain access to the retinal detachment or tear. The surgeon may also use the vitrectomy probe, scissors, a pick, and/or forceps to remove any membrane that has contributed to the retinal detachment or tear. During this portion of the surgery, a saline solution is typically infused into the eye via the infusion cannula to maintain the appropriate intraocular pressure.

Next, the surgeon must manipulate the detached or torn portion of the retina to flatten against the choroid in the proper location. A soft tip cannula, forceps, or pick is typically utilized for such manipulation. Many surgeons also inject perfluorocarbon liquid as a retinal tamponading fluid into the posterior segment of the eye while aspirating the saline solution in the posterior segment to help cause the detached or torn portion of the retina to flatten against the choroid in the proper location. This procedure is typically referred to as a "fluid/perfluorocarbon" exchange. Other surgeons inject air as a retinal tamponading fluid into the posterior segment of the eye while aspirating the saline solution. This procedure is typically referred to as a "fluid/air" exchange. Finally, other surgeons inject a mixture of air and a gas such as $SF_6$, $C_3F_8$, or $C_2F_6$ as a retinal tamponading fluid into the posterior segment of the eye while aspirating the saline solution. This procedure is typically referred to as a "fluid/gas" exchange. As used herein, a "fluid" may include any liquid or gas that is suitable for use in the eye, including, but not limited to, saline solution with or without additives, silicone oil, a perfluorocarbon liquid, air, or a perfluorocarbon gas.

After performing one of the above-described "fluid/fluid" exchanges, the surgeon then typically drains any sub-retinal fluid present between the retina and the choroid. Conventionally, the vacuum port of a vitrectomy probe; a blunt tipped, straight cannula having a port on its distal tip; blunt-tipped cannulas or sharp-tipped needles having a straight proximal portion, an angulated or slanted distal portion, and a port on their distal tips; and a soft tip, cannulated flute needle have all been used to drain subretinal fluid. The literature also mentions a curved cannula having a radius of curvature of the human eye and a single port on its ventral surface near its tip for the drainage of subretinal fluid. The literature further mentions a curved cannula having a radius of curvature of the human eye, a port on its ventral surface near its tip for the drainage of subretinal fluid, and a second port on its dorsal surface spaced away from its tip for supporting a "fluid/gas" exchange. Such instruments may be connected to a conventional syringe, a flute needle handle, or to an aspiration port of a surgical cassette that is operatively coupled to an ophthalmic surgical console. Such instruments gain access to the subretinal space via an existing retinal tear, a surgical excision of a piece of retina (retinectomy), or a surgical incision through the retina (retinotomy). After the detached or torn portion of the retina is properly located and the subretinal fluid is drained, the surgeon typically uses a diathermy probe or a laser to create a scar that, when healed, holds portions of the detached retina in place.

The above-described instruments used to drain subretinal fluid all suffer from certain disadvantages. As these instruments aspirate sub-retinal fluid, they often incarcerate the retina into their ports. These instruments also sometimes cause avulsion of parts of the retinal pigment epithelium. Further, these instruments sometimes cause mechanical damage to the choriocapillaris and choroid, causing bleeding that further complicates retinal reattachment and further obscures the visual field.

Therefore, a need exists in vitreoretinal surgery for an improved instrument for removing subretinal fluid and performing fluid exchanges in vitreoretinal surgery. The instrument should be easy for the surgeon to use, should maximize patient safety, and should be economically feasible.

SUMMARY OF THE INVENTION

One aspect of the present invention comprises a vitreoretinal instrument including a handle and a cannula coupled to the handle. The cannula includes a curved distal portion. The curved distal portion has a side port for disposing in a subretinal space and for aspirating subretinal fluid. The cannula also includes a second port disposed sufficiently away from the side port so that the second port may be used for aspirating a second fluid from the vitreous cavity without removing the first port from the subretinal space.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

Figure 1:
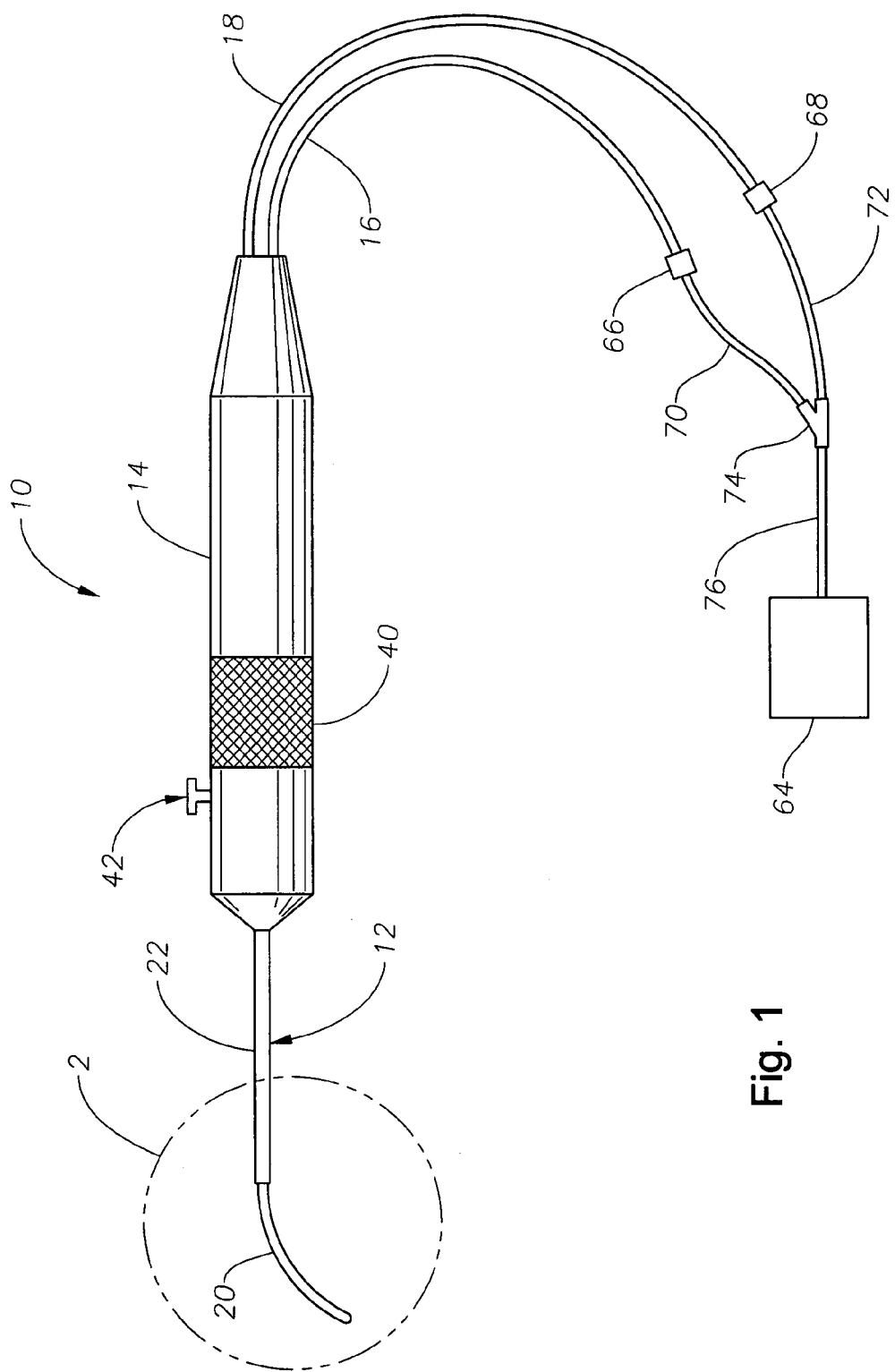
FIG. 1 is a side view of an instrument according to a preferred embodiment of the present invention.
Figure 2:
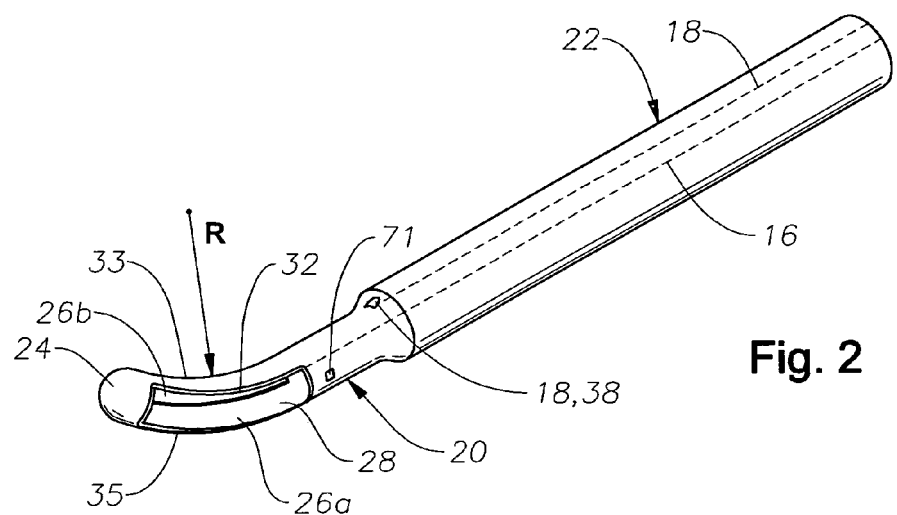
FIG. 2 is an enlarged, perspective, schematic view of the cannula of the instrument of FIG. 1 taken at circle 2 in FIG. 1.
Figure 3:
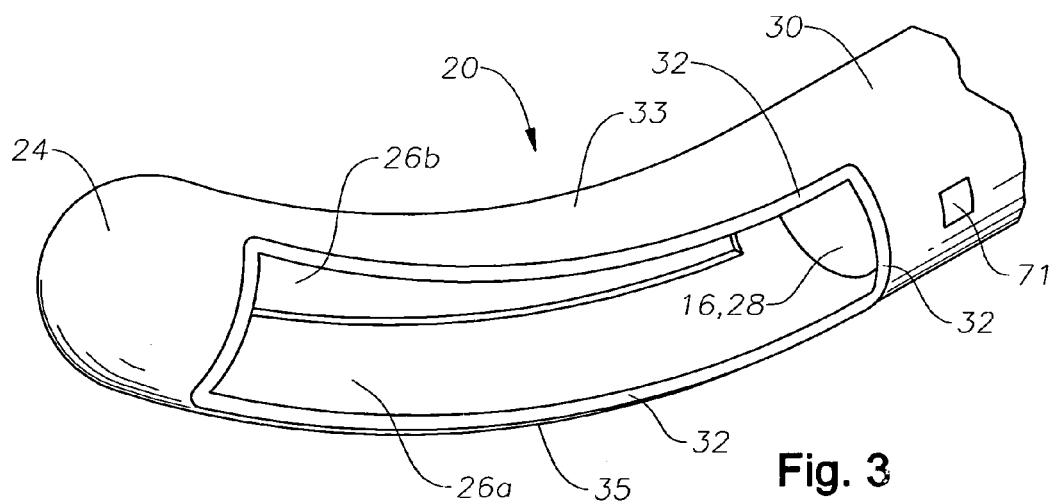
FIG. 3 is an enlarged, perspective, schematic view of the curved portion of the cannula of FIG. 2.
Figure 4:
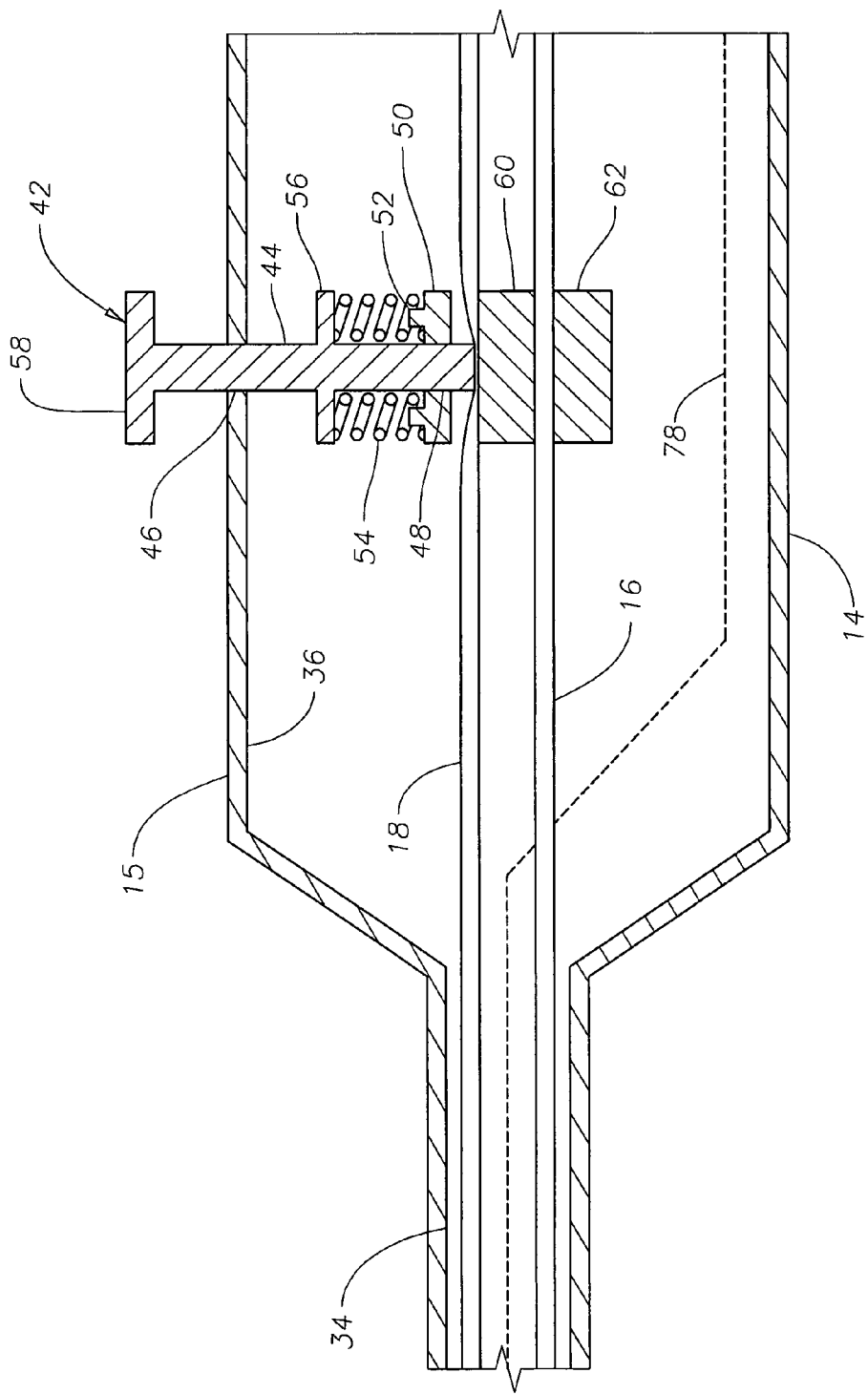
FIG. 4 is an enlarged, side, cross-sectional view of a portion of the instrument of FIG. 1.

The preferred embodiments of the present invention and their advantages are best understood by referring to FIGS. 1 through 4 of the drawings, like numerals being used for like and corresponding parts of the various drawings.

Instrument 10 generally includes a cannula 12 on its distal end, a handle 14, and flexible tubing 16 and 18 extending from its proximal end. Cannula 12 preferably includes a curved, distal portion 20 and a straight, proximal portion 22. Curved portion 20 preferably has a radius of curvature R substantially equal to the radius of curvature of the human eye. Curved portion 20 also preferably has a closed tip 24 having a smooth, convex surface for interfacing with the retina. Alternatively, closed tip 24 may have a sharpened, needle-like tip. Curved portion 20 also has dual side ports 26a and 26b that open to a lumen 28 of cannula 12. Side ports 26a and 26b are preferably fluidly coupled and are disposed at an angle of about 90 degrees from the plane of curvature of curved portion 20. Side ports 26a and 26b are preferably slightly recessed from an exterior surface 30 of curved portion 20 and preferably each have a raised ridge 32 around their peripheries. Such recession and ridge 32 prevent or reduce the likelihood of retina, retinal pigment epithelium, or choroid incarceration within side port 26a or 26b. Curved portion 20 has a ventral surface 33 and a dorsal surface 35. Curved portion 20 is preferably made of a flexible thermoplastic such as a polyamide. Curved portion 20 may alternatively be made of a metal such as stainless steel.

Straight portion 22 is preferably about 20 to about 25 gauge and is preferably made of a metal such as stainless steel. Straight portion 22 has a lumen 34 that is coupled to lumen 28 of curved portion 20 on its distal end and to a lumen 36 of handle 14 on its proximal end. Straight portion 22 preferably has a port 38 opening onto its exterior surface and extending into lumen 34. Port 38 is preferably disposed at the juncture of curved portion 20 and straight portion 22.

Handle 14 preferably includes a roughened, textured, or knurled surface 40 to facilitate a surgeon grasping handle 14 between his or her thumb and index fingers using a pencil-like grip. Handle 14 also preferably includes a compression valve 42 for actuation by the tip of the surgeon's middle finger. Compression valve 42 preferably includes a piston 44 that is slidably disposed within an aperture 46 of a body 15 of handle 14 and an aperture 48 within a spring stop 50 disposed within lumen 36 of handle 14. Spring stop 50 includes an annular spring seat 52 holding a spring 54 that biases piston 44 toward aperture 46 by exerting a force against a spring flange 56 of piston 44. Compression valve 42 also includes an actuating surface 58 for interfacing with a surgeon's finger.

Flexible tubing 16 is disposed within lumen 36 between tubing support members 60 and 62. Flexible tubing 18 is disposed within lumen 36 between spring stop 50 and tubing support member 60. Spring stop 50, tubing support member 60, and tubing support member 62 are supported by body 15 of handle 14. Flexible tubing 16 and 18 are also disposed within lumens 34 and 28 of straight portion 22 and curved portion 20, respectively. A distal end of tubing 16 is fluidly coupled to side ports 26a and 26b of curved portion 20. A distal end of tubing 18 is fluidly coupled to port 38 of straight portion 22. The proximal ends of tubing 16 and 18 are each fluidly coupled to a source of vacuum 64 via connectors 66 and 68, respectively. Vacuum source 64 is schematically illustrated in FIG. 1. Preferably, vacuum source 64 is disposed within an ophthalmic surgical console, and may provide fixed vacuum or vacuum that varies proportionally with the position of a footswitch operatively coupled to the ophthalmic surgical console. In this case, flexible tubing 70, 72, and 76 and Y-fitting 74 may be used to fluidly couple connectors 66 and 68 to the vacuum port of a surgical cassette operatively coupled to the ophthalmic surgical console in the conventional manner. Alternatively, Y-fitting 74 may be removed and connectors 66 and 68 may be fluidly coupled to separate vacuum ports of such a surgical cassette. In addition, one or more conventional syringes may be utilized as vacuum source 64.

The following describes a preferred procedure whereby a surgeon may use instrument 10 to drain subretinal fluid and perform a fluid exchange in vitreoretinal surgery. After performing a vitrectomy to gain access to the retinal detachment or tear, instrument 10 is fluidly coupled to vacuum source 64 as described above. The surgeon positions instrument 10 within the eye so that ventral surface 33 of curved portion 20 is disposed closest to the retina, dorsal surface 35 of curved portion 20 is disposed closest to the choroid, side ports 26a and 26b are disposed under the retina in the subretinal space, and port 38 is disposed above the retina in the vitreous cavity. Access for curved portion 20 into the subretinal space may be gained through the pre-existing retinal break or tear, or via a retinectomy or retinotomy. If tip 24 is formed with a sharpened tip, it may be used to perform such retinectomy or retinotomy. The surgeon presses down on actuating surface 58 of compression valve 42 with his or her middle finger so that piston 44 closes flexible tubing 18 against tubing support member 60 and precludes aspiration from port 38. The surgeon then activates vacuum source 64 and aspirates subretinal fluid via side ports 26a and 26b and tubing 16. Alternatively, the surgeon may simply passively drain the subretinal fluid via side ports 26a and 26b due to the difference between the intraocular pressure and the pressure within tubing 16. When the subretinal fluid egress progresses to a point that the size of the retinal detachment is no longer decreasing, the surgeon begins to perform a fluid/perfluorocarbon, fluid/air, or fluid/gas exchange to replace the saline solution within the eye with an appropriate retinal tamponading fluid to help cause the detached or torn portion of the retina to flatten against the choroid in the proper location. To perform such fluid/fluid exchange, the surgeon releases the pressure on actuating surface 58 of compression valve 42. Spring 54 upwardly biases piston 44 to open flexible tubing 18 and provide vacuum to port 38, aspirating the saline solution. Aspiration of any subretinal fluid continues via side ports 26a and 26b and tubing 16. The surgeon injects a retinal tamponading fluid (liquid, air, or gas) into the eye via an infusion cannula inserted through a scleratomy. By draining the subretinal fluid and performing the fluid/fluid exchange without having to remove instrument 10 from the subretinal space to insert an aspiration probe to drain the saline solution, fluid recirculation from the vitreous cavity through the retinal tear is prevented and complete drainage of subretinal fluid is achieved. Instrument 10 also prevents such posterior recirculation of fluid into the subretinal space that occurs if the fluid/fluid exchange is preformed prior to draining subretinal fluid.

The surgeon may also use tip 24, ventral surface 33, and/or dorsal surface 35 of curved portion 20 to express subretinal fluid, mobilize and/or smooth out retinal folds, unfold retinal tears and/or retinectomy flaps, or help to cause the retina to flatten against the choroid in the proper location. The surgeon may move handle 14 using a "squeegee-like" motion when utilizing dorsal surface 35 for such purposes.

The surface of tip 24, as well as ventral surface 33 and dorsal surface 35, are very smooth and have very low friction to avoid damage to the retina. In addition, the surface of tip 24, as well as ventral surface 33 and dorsal surface 35, may be coated with or made from Teflon, silicone, or other friction reducing material to avoid adherence to the retina, retinal pigment epithelium, or choroid. In addition, an optical fiber 78 may be disposed in handle 14 and straight portion 22 so as to terminate in curved portion 20. In this case, curved portion 20 may be formed with a light transmitting window 71, or may be formed from a light transmitting plastic, so that instrument 10 can provide intraocular illumination for the surgeon when fiber 78 is operatively coupled to a light source. Such illumination allows the surgeon to hold a microsurgical instrument other than an endoilluminator with his or her other hand, if desired. Such light transmitting window 71 or light transmitting plastic are preferably substantially transparent.

From the above, it may be appreciated that the present invention provides improved apparatus and methods for removing subretinal fluid and performing fluid exchanges in vitreoretinal surgery. The instrument is easy for a surgeon to use and may be made in an economical manner. The instrument maximizes patient safety as well as the success of the surgical procedure by facilitating complete removal of subretinal fluid; preventing or reducing the likelihood of retina, retinal pigment epithelium, or choroid damage, and facilitating the proper repositioning of retinal tears or detachments.

The present invention is illustrated herein by example, and various modifications may be made by a person of ordinary skill in the art. For example, although compression valve 42 is described hereinabove with piston 44 compressing flexible tubing 18 and precluding aspiration by port 38 when a surgeon presses down on actuating surface 58 with his or her finger, compression valve 42 may also be designed so that piston 44 compresses tubing 18 and precludes aspiration by port 38 when piston 44 is in its undepressed position. In this case, aspiration by port 38 is provided when the surgeon presses down on actuating surface 58. As another example, a different valve other than a compression valve may be used for valve 42. As a further example, the present invention may also be used to perform air/gas exchanges typically performed in vitreoretinal surgery. As a further example, either or both of side ports 26a and 26b and port 38 could be utilized to inject a surgical fluid or drug formulation, if desired. As a further example, the present invention is also applicable to other types of surgeries other than vitreoretinal surgery.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of draining fluid from a subretinal space of an eye and performing a fluid exchange in a vitreous of said eye, comprising the steps of:
   providing a vacuum source;
   providing an vitreoretinal instrument, comprising:
      a handle; and
      a cannula coupled to said handle comprising:
         a curved distal portion having a plane of curvature and a side port disposed at an angle of about 90 degrees to said plane of curvature;
         a second port disposed away from said side port;
         a first flexible tubing having a distal end fluidly coupled to said side port and a proximal end fluidly coupled to said vacuum source;
         a second flexible tubing having a distal end fluidly coupled to said second port and a proximal end fluidly coupled to said vacuum source; and
         a valve disposed on said handle for selectively opening and closing said second flexible tubing;
   grasping said handle;
   disposing said cannula within said eye so that said side port is in said subretinal space and said second port is in said vitreous above said subretinal space;
   actuating said valve to close said second flexible tubing;
   activating said vacuum source;
   aspirating fluid from said subretinal space via said side port and said first flexible tubing;
   actuating said valve to open said second flexible tubing; and
   aspirating said fluid from said vitreous via said second port and said second flexible tubing while continuing to perform said step of aspirating fluid from said subretinal space.

2. The method of claim 1 wherein said step of disposing said cannula further comprises disposing said cannula so that a ventral surface of said cannula is closest to said retina and a dorsal surface of said cannula is closest to said choroid.

3. The method of claim 1 wherein said step of actuating said valve is performed when a user of said instrument observes that a size of a retinal detachment or a retinal tear in said eye ceases decreasing due to said step of aspirating fluid from said subretinal space.

4. The method of claim 1 wherein said side port prevents incarceration of said retina into said side port.

5. The method of claim 1 wherein said cannula comprises a second side port disposed at an angle of about 6 degrees to said plane of curvature and opposite said first side port.

6. The method of claim 1 further comprising the steps of:
   disposing an infusion cannula within said vitreous; and
   injecting a retinal tamponading fluid into said vitreous via said infusion cannula.

7. A method of draining fluid from a subretinal space of an eye and performing a fluid exchange in a vitreous of said eye, comprising the steps of:
   providing a vacuum source;
   providing an vitreoretinal instrument, comprising:
      a handle; and
      a cannula coupled to said handle comprising:
         a curved distal portion having a plane of curvature and a side port disposed at an angle of about 90 degrees to said plane of curvature;
         a second port disposed away from said side port;
         a first flexible tubing having a distal end fluidly coupled to said side port and a proximal end fluidly coupled to said vacuum source;
         a second flexible tubing having a distal end fluidly coupled to said second port and a proximal end fluidly coupled to said vacuum source; and
         a valve disposed on said handle for selectively opening and closing said second flexible tubing;
   grasping said handle;
   disposing said cannula within said eye so that said side port is in said subretinal space and said second port is in said vitreous above said subretinal space;
   actuating said valve to close said second flexible tubing;

passively draining fluid from said subretinal space via said side port and said first flexible tubing;
activating said vacuum source;
actuating said valve to open said second flexible tubing; and
aspirating said fluid from said vitreous via said second port and said second flexible tubing while aspirating said fluid from said subretinal space via said side port and said first flexible tubing.

8. The method of claim 7 wherein said step of disposing said cannula further comprises disposing said cannula so that a ventral surface of said cannula is closest to said retina and a dorsal surface of said cannula is closest to said choroid.

9. The method of claim 7 wherein said step of actuating said valve is performed when a user of said instrument observes that a size of a retinal detachment or a retinal tear in said eye ceases decreasing due to said step of passively draining fluid from said subretinal space.

10. The method of claim 7 wherein said side port prevents incarceration of said retina into said side port.

11. The method of claim 7 wherein said cannula comprises a second side port disposed at an angle of about 90 degrees to said plane of curvature and opposite said first side port.

12. The method of claim 7 further comprising the steps of:
disposing an infusion cannula within said vitreous; and
injecting a retinal tamponading fluid into said vitreous via said infusion cannula.

* * * * *